US006043590A

United States Patent [19]

Gilmore

[11] Patent Number: 6,043,590

[45] Date of Patent: Mar. 28, 2000

[54] COMPOSITE TRANSDUCER WITH CONNECTIVE BACKING BLOCK

[75] Inventor: James Michael Gilmore, Bothell, Wash.

[73] Assignee: ATL Ultrasound, Bothell, Wash.

[21] Appl. No.: 08/840,470

[22] Filed: Apr. 18, 1997

[51] Int. Cl.[7] .............................. H01L 41/47; A61B 8/00

[52] U.S. Cl. ............................................ 310/367; 310/334

[58] Field of Search .................................... 310/237, 331, 310/335, 322, 334, 367

[56] References Cited

U.S. PATENT DOCUMENTS

| | | | |
|---|---|---|---|
| 2,881,336 | 4/1959 | Elion | 310/8.2 |
| 4,398,325 | 8/1983 | Piaget et al. | 310/334 |
| 4,404,489 | 9/1983 | Larson, III et al. | 310/334 |
| 4,616,152 | 10/1986 | Saito et al. | 310/334 |
| 4,747,192 | 5/1988 | Rokurota | 29/25.35 |
| 4,751,420 | 6/1988 | Gebhardt et al. | 310/327 |
| 4,825,115 | 4/1989 | Kawabe et al. | 310/327 |
| 4,894,895 | 1/1990 | Rokurohta et al. | 29/25.35 |
| 4,962,332 | 10/1990 | Rokurohta et al. | 73/632 |
| 5,065,068 | 11/1991 | Oakley | 310/357 |
| 5,115,810 | 5/1992 | Wantanabe et al. | 128/662.03 |
| 5,164,920 | 11/1992 | Bast et al. | 367/140 |
| 5,267,221 | 11/1993 | Miller et al. | 367/140 |
| 5,329,498 | 7/1994 | Greenstein | 367/155 |
| 5,434,827 | 7/1995 | Boloforosh | 310/320 |
| 5,539,965 | 7/1996 | Safari et al. | 29/25.35 |
| 5,625,149 | 4/1997 | Gururaja et al. | 310/334 |
| 5,637,800 | 6/1997 | Finsterwald et al. | 73/642 |
| 5,706,820 | 1/1998 | Hossack et al. | 128/662.03 |
| 5,796,207 | 8/1998 | Safari et al. | 310/334 |
| 5,810,009 | 9/1998 | Mine et al. | 310/334 |

*Primary Examiner*—Thomas M. Dougherty
*Attorney, Agent, or Firm*—W. Brinton Yorks, Jr.

[57] ABSTRACT

A backing block for an ultrasonic array transducer comprises a flex circuit embedded in a body of acoustic backing material, with conductive traces on the flex circuit terminating at the surface of the body at which an array transducer is mounted and extending out from the rear of the body for connection to electrical circuitry. The array transducer is formed of a composite material in which the pattern of the composite material is oriented at an oblique angle to the kerfs of the transducer.

11 Claims, 11 Drawing Sheets

COMPOSITE TRANSDUCER WITH CONNECTIVE BACKING BLOCK

This invention relates to ultrasonic transducers, and in particular to composite transducer arrays and acoustic backing blocks with integral conductors for a transducer array.

An ultrasonic transducer probe is used by an ultrasound system as the means of transmitting acoustic energy into the subject being examined, and receiving acoustic echoes returning from the subject which are converted into electrical signals for processing and display. Transducer probes may use either single element or multi-element piezoelectric components as the sound transmission and/or reception devices. A multi-element ultrasonic transducer array is generally formed from a bar or block of piezoelectric material, which may be either a ceramic or a polymer. The bar or block is cut or diced into one or more rows of individual elements to form the array. The element-to-element spacing is known as the "pitch" of the array and the spaces between individual elements are known as "kerfs." The kerfs may be filled with some filler material, generally a damping material having low acoustic impedance that blocks and absorbs the transmission of vibrations between adjoining elements, or they may be air-filled. The array of elements may be left in a linear configuration in which all of the elements are in a single plane, or the array may be bent or curved for use as a convex or concave array.

Before the piezoelectric material is diced into individual array elements it is generally coated with metallic electrode material on the top (also referred to as the front, or transmit/receive side) and bottom of the bar. The electrodes on the top of the elements are conventionally connected to an electrical reference potential or ground, and individual conductors are attached to electrode areas on the bottom of the bar to electrically connect to each subsequently formed element. These conductors are then conventionally potted in an acoustic backing material as described, for example, in U.S. Pats. No. 4,825,115 (Kawabe et al.) which fills the space below the transducer elements and between the wires, and damps acoustic vibrations emanating from the bottom of the transducer array. Alternately, the conductors and backing material may be preformed in a block of backing material containing parallel spaced wires which is then attached to the piezoelectric as described in U.S. Pat. No. 5,329,498 (Greenstein) and U.S. Pat. No. 5,267,221 (Miller et al.). The piezoelectric bar and electrodes are then diced while attached to the backing material. As the bar is diced into individual elements the metal plating is simultaneously cut into individual electrically separate electrodes for each transducer element.

These techniques for forming a transducer array with its electrical connections and backing present various drawbacks in their implementation. The technique described by Kawabe et al. requires that conductors be cut, folded and cast in backing material, all while attached to the transducer ceramic, posing a heightened risk of damaging the ceramic during any of these processing steps. Greenstein and Miller et al. avert this risk by precasting a backing block with embedded conductors oriented in precise alignment with the transducer elements, but provide no guidance on forming such a finely drawn structure easily or inexpensively. Accordingly, it is desirable to be able to fabricate an array transducer easily and inexpensively without a substantial hazard to the transducer ceramic.

In accordance with the principles of the present invention, a monolithic conductive backing is provided for an ultrasonic array transducer. The conductors for the backing are formed on a flexible circuit board to the desired transducer element pitch. The flex circuit is cast in backing material with the distal ends of the conductors extending to the surface of the backing surface which connects to the array transducer, and the proximal end of the flex circuit extending from the backing material. The distal ends of the conductors provide electrical connection to the attached array transducer, and the elements can be connected to transmit/receive circuitry by connecting to the conductors of the proximally extending flex circuit.

In a preferred embodiment the transducer array is a convex curved array. Preferably the array is formed of a bar of composite material which will conform to the curvature of the array, and with a composite pattern oriented at an oblique angle to the kerfs of the array. The preferred embodiment makes it possible to dice the piezoelectric bar into elements after it is formed into a curve and attached to the backing, and provides high performance through suppression of undesired modes of resonance and low acoustic impedance.

Figure 5B:
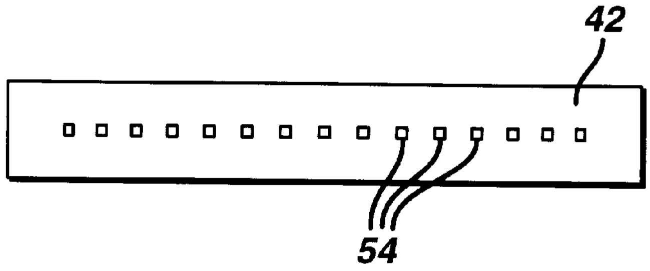
Figure 5A:
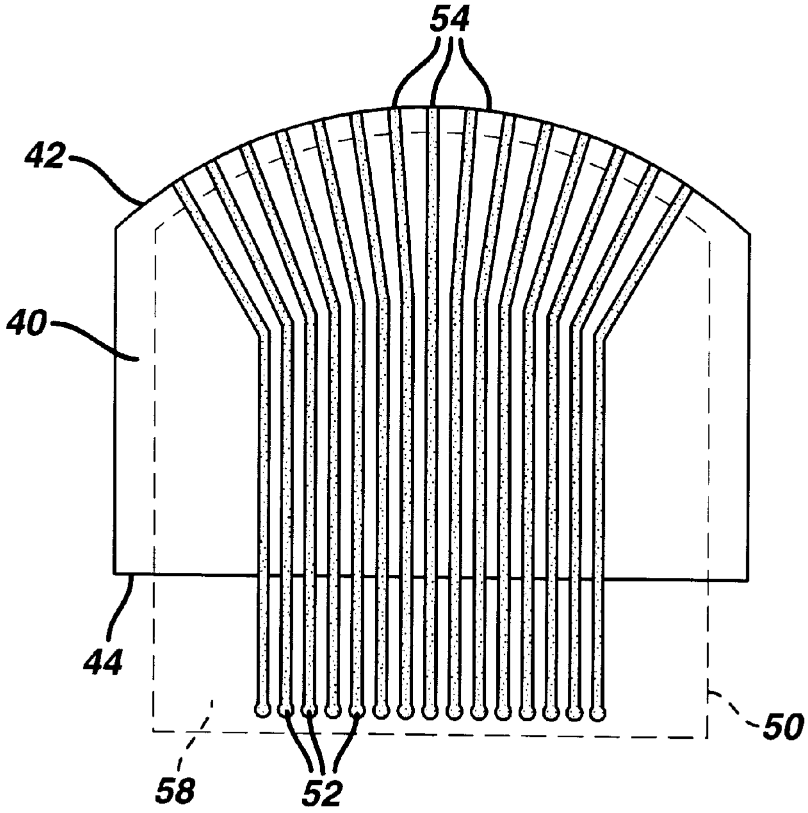
Figure 6B:
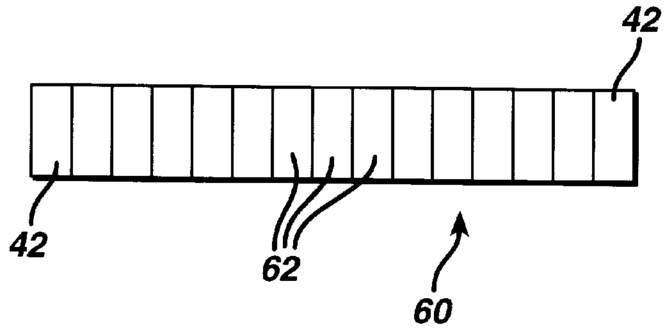
Figure 6A:
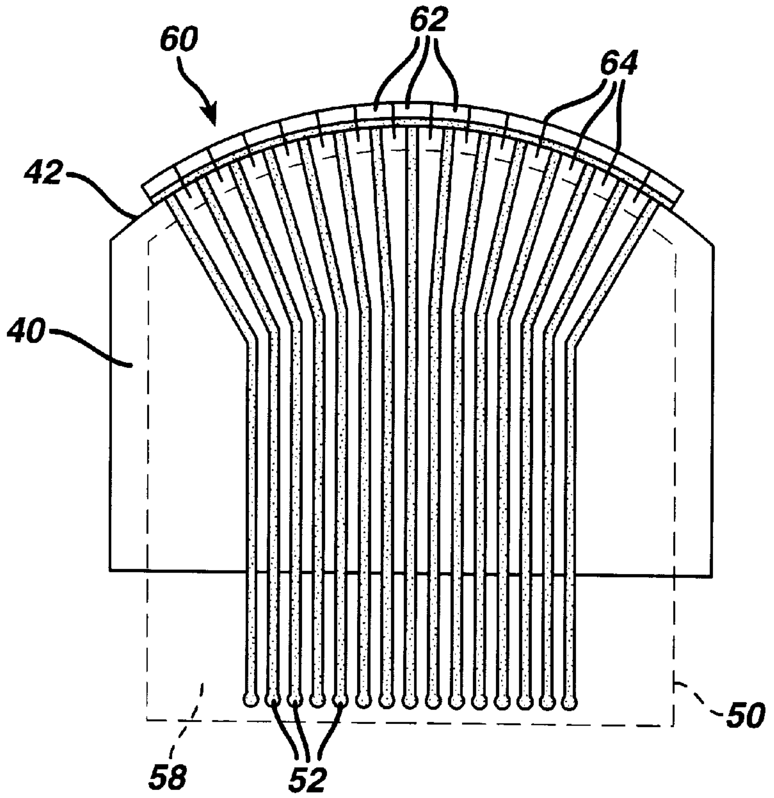
Figure 7A:
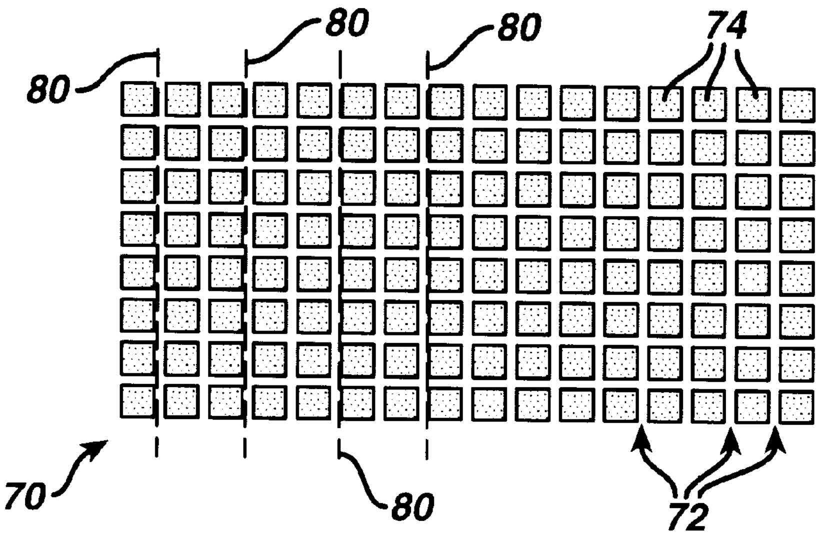
Figure 7B:
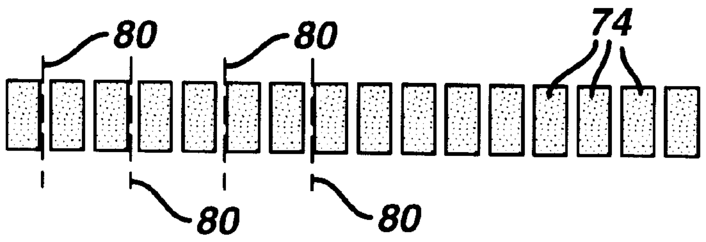
Figure 8:
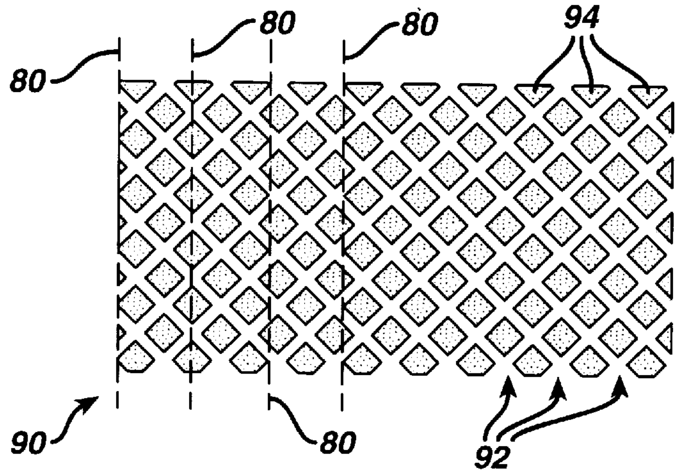
Figure 9:
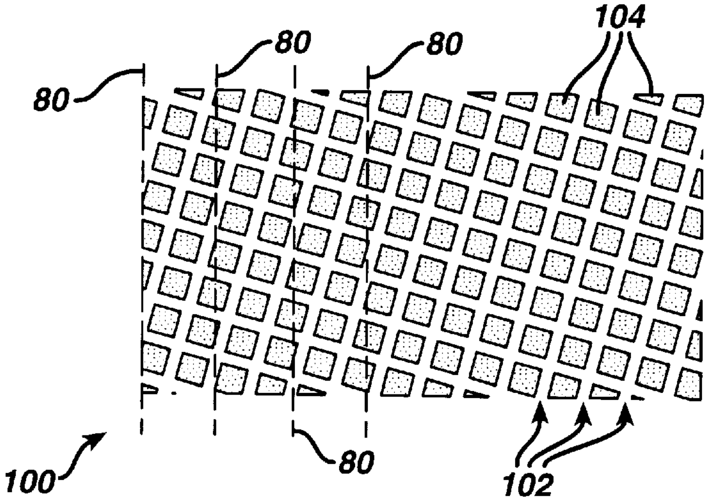
Figure 10A:
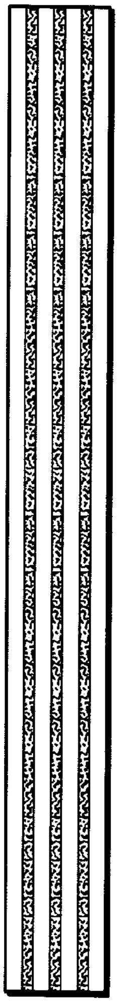
Figure 10B:
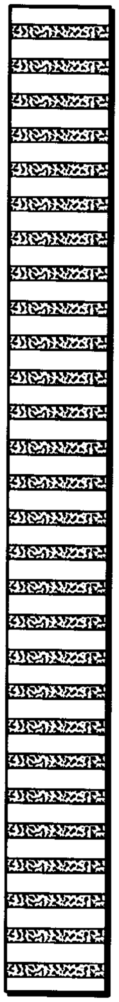

FIGS. 5*a* and 5*b* are two views of a backing block of a preferred embodiment of the present invention;

FIGS. 6*a* and 6*b* are two views of the backing block of FIGS. 5*a* and 5*b* when attached to a convex transducer array;

FIGS. 7*a* and 7*b* are top plan and side views of a 1–3 composite piezoelectric array of the prior art;

FIGS. 8 and 9 are top plan views of a 1–3 composite piezoelectric array of the present invention;

FIGS. 10*a* and 10*b* illustrate two 2—2 composite piezoelectric array elements of the prior art;

FIGS. 11*a*, 11*b*, 11*c*, and 12 illustrate 2—2 composite piezoelectric array elements of the present invention; and FIGS. 13*a*–13*d* illustrate a transducer array of the present invention during various stages of its assembly.

Figure 1:
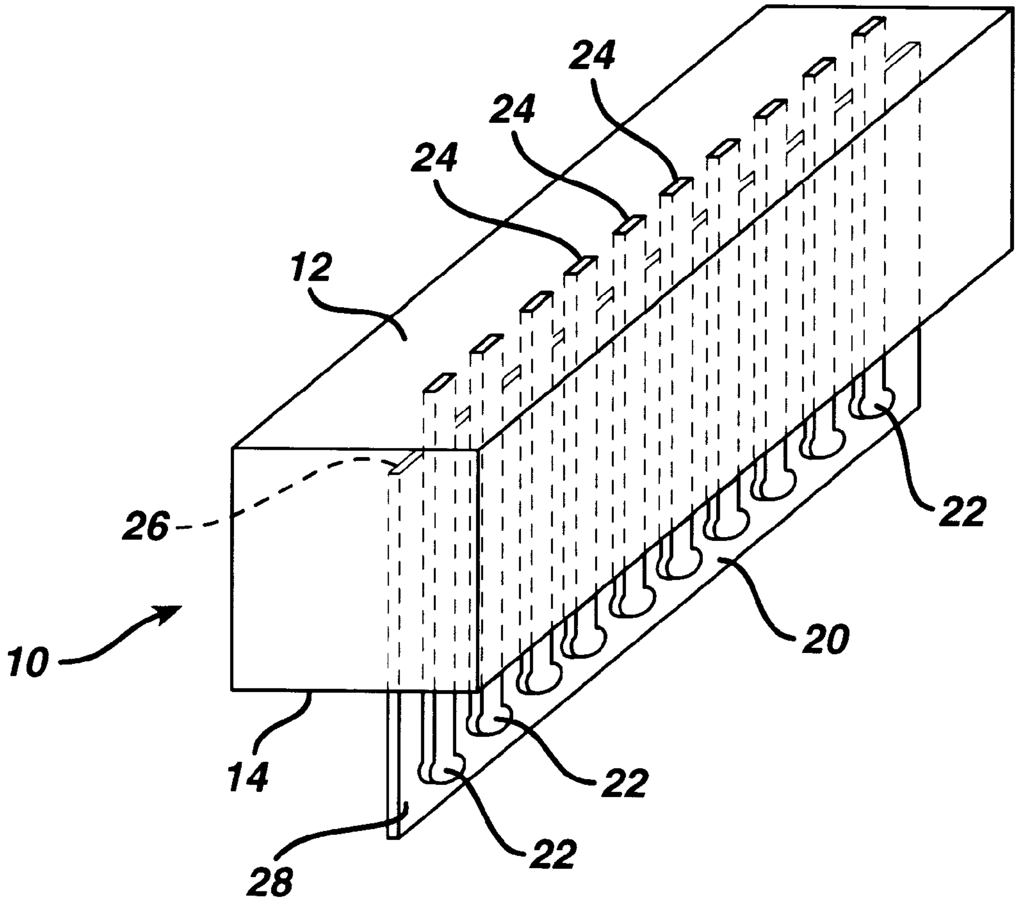
FIG. 1 illustrates a monolithic connective backing block of the present invention.

Referring first to FIG. 1, a monolithic connective backing block 10 for a transducer array constructed in accordance with the principles of the present invention is shown. The backing block is formed of a material with relatively low acoustic impedance and high acoustic attenuation. A suitable material is a filled epoxy or urethane composite. The fillers may be metallic particles such as tungsten or silver, oxide powders, or microballoons. The filler may be blended with the epoxy or urethane under pressure to assure uniformity, the desired impedance, and the proper attenuation.

The backing block 10 has a distal or top surface 12 to which a piezoelectric transducer array attaches. The backing block 10 has a rear or bottom surface 14 from which a flexible circuit board 20 extends. The flex circuit 20 is formed of a sheet 28 of flexible nonconductive material such as Kapton. Formed on the sheet 28 by etching or photolithography is a series of conductive traces 22 formed of, for example, copper. The conductive traces are formed with a lateral spacing which matches the pitch of the elements of the transducer array. The distal ends 24 of the conductive traces are flush with the distal surface 12 of the backing block, where they will align and make electrical contact with the elements of an attached transducer array. At their proximal ends at the bottom of the backing block the conductive traces can be connected to electrical circuitry which interacts with the transducer elements, such as transducer drivers, receivers, tuning elements, or multiplexers.

In a preferred embodiment, the flexible sheet 28 does not extend to the surface 12 of the backing block alongside the conductive traces. Instead, the distal edge 26 of the sheet 28 terminates inside the backing block and short of the surface 12. This eliminates the possibility of contamination of the distal ends of the conductive traces with adhesives and particulate matter from the flexible sheet.

Figure 2:
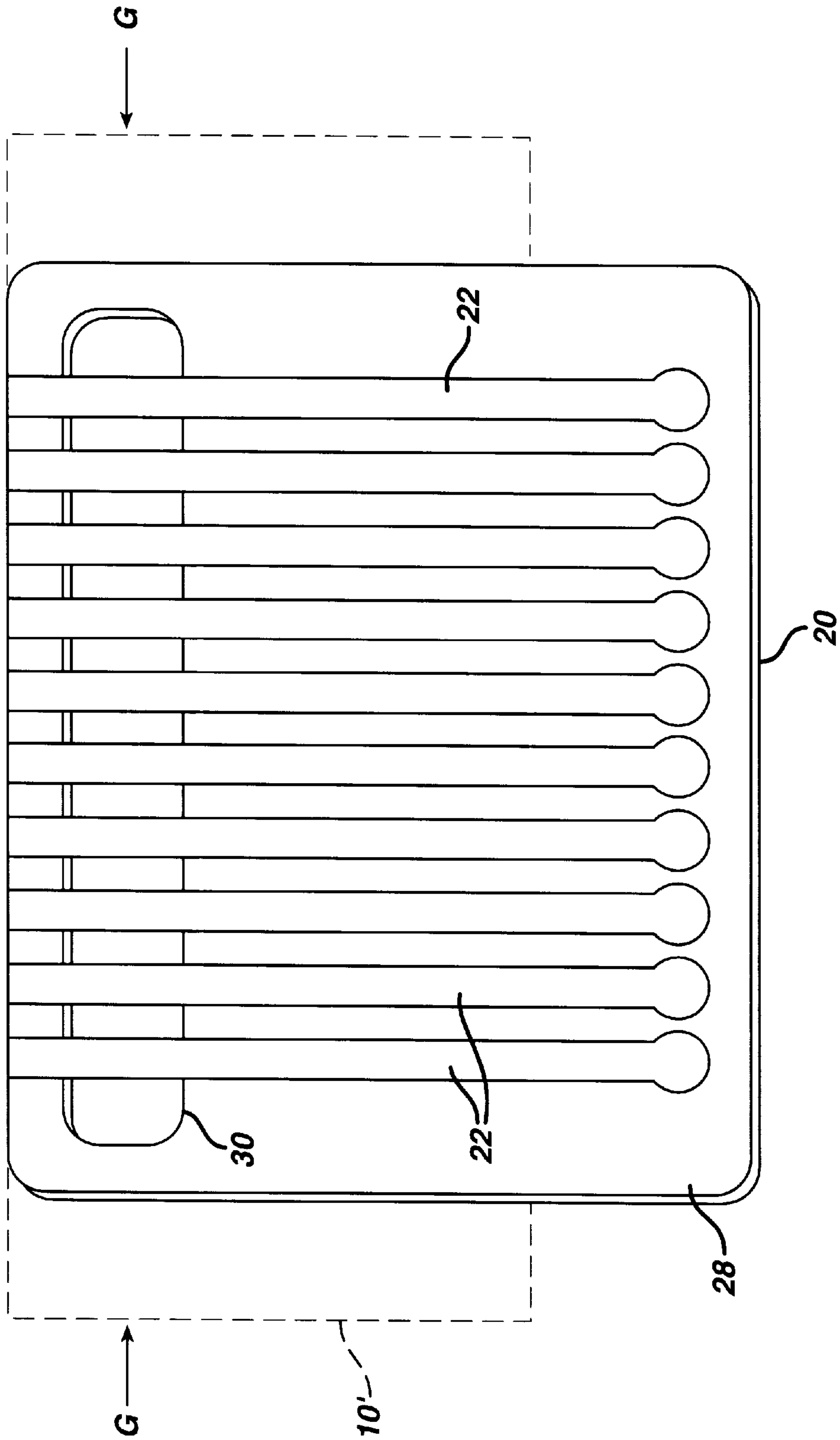
FIG. 2 illustrates the flexible circuit board of the backing block of FIG. 1.
Figure 3:
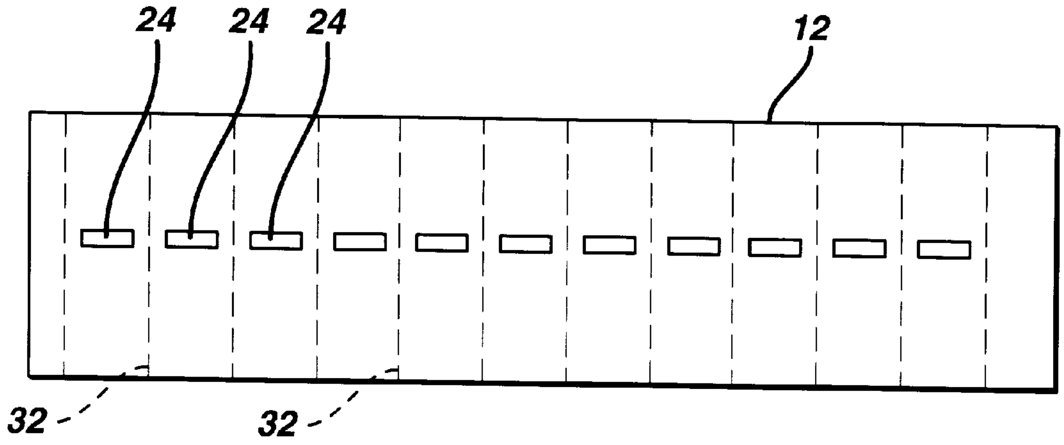
FIG. 3 is a plan view of the distal surface of the backing block of FIG. 1.

A plan view of the initial flex circuit 20 of a preferred embodiment of the present invention is shown in FIG. 2. In this embodiment an aperture or window 30 has been etched through the flexible sheet 28 behind the conductive traces 22. The conductive traces remain fixed in their desired parallel orientation and spacing, which matches the array pitch, since the traces remain attached to the sheet 28 on either side where they bridge the window 30. To form the backing block of FIG. 1, the backing material is cast around the flex circuit 20 as indicated by the outline 10'. After the backing material has cured, the distal end of the block is ground and lapped down to the level indicated by opposing arrows G, with reference to tooling fixtures on the block (not shown). This process removes the portion of the sheet 28 above the window 30, leaving the distal ends of the traces 22 flush with the finished distal end of the block and "flying", that is, with no adjacent flex board material. FIG. 3 is a plan view of the distal surface 12 of the finished backing block, with the distal ends 24 of the conductive traces 22 shown in alignment between the locations 32 of the kerfs of the transducer array elements.

Figure 4:
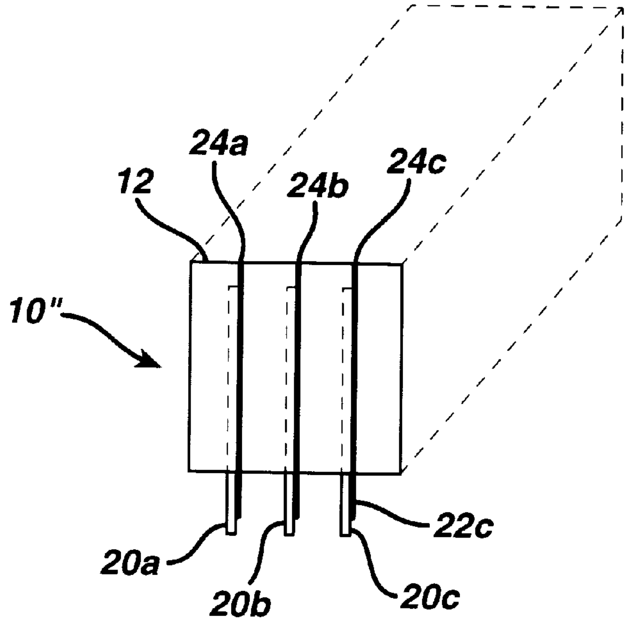
FIG. 4 illustrates a connective backing block of the present invention suitable for use with a two dimensional transducer array.

This inventive technique for forming a transducer backing block with precisely aligned conductors is readily suited for use with a two dimensional array of transducer elements as shown by the end view of the backing block 10" of FIG. 4. As there shown, three flex circuits **20*a*, 20*b*, and 20*c* are embedded in the backing material of the block. Three rows of the ends of separate conductive traces 24*a*, 24*b*, and 24*c* are thus formed at the distal surface 12** of the block. This embodiment will provide separate electrical connections to an attached transducer array of three rows of transducer elements along the length of the block.

It will be understood that, while the above embodiments are illustrated with ten conductive traces, a constructed embodiment will have 128 or more conductive traces for transducer of 128 or more elements in a row.

FIGS. **5*a* and 5*b* illustrate a preferred embodiment of the present invention. In this embodiment a flex circuit 50 has its conductive traces 52 arranged on the Kapton sheet 58 in a fanning pattern which that the distal ends 54 of the traces are evenly distributed along the arcuate distal surface 42 of the backing block 40, as shown in the top view of the surface 42 in FIG. 5*b*. The arcuate distal surface is formed by cylindrically grinding this surface to the desired radius of curvature. As before, the proximal end of the flex circuit 50 extends from the proximal end 44 of the backing block 40** for attachment to other circuitry.

In FIG. **6*a*, a curved transducer array 60 is adhesively attached to the distal surface 42 of the block 40, with individual transducer elements 62 aligned with the distal ends of the conductive traces. The kerfs between the transducer elements 62 are indicated at 64. FIG. 6*b* is a top plan view of the assembly shown with the transducer array 60 attached in place. The conventional way to prepare the transducer array is to cut a bar of piezoelectric ceramic to the desired dimensions of the array, attach the bar to a flexible backing, then dice the individual elements of the array. Once the bar has been cut into separate elements, the array can be curved on a mandrel to the desired arc of curvature and then affixed to the backing 40**.

In accordance with the principles of a further aspect of the present invention, the transducer array is formed of a composite piezoelectric material. A composite transducer is formed by subdicing a bar of piezoelectric material into many fine subelements, then filling in the kerfs between the subelements with a kerf filler such as an epoxy or urethane. Rather than exhibit the properties of unitary elements of piezoelectric, the composite transducer will exhibit the properties of the subelements in the aggregate. This allows a designer to control characteristics of the transducer such as the acoustic impedance. And formed as it is of a matrix of piezoelectric subelements and filler, the composite transducer can be conformed to the desired arcuate shape before it has been diced into individual transducer elements.

A portion of a typical composite transducer array 70 is shown in top plan and side views in FIGS. **7*a* and 7*b*. A bar of piezoelectric ceramic has been subdiced into many small subelements or pillars 74. The interstices 72 between the pillars 74 are filled with an epoxy filler. The illustrated composite material is termed a 1–3 composite, where "1" indicates the number of directions in which the piezoelectric is continuous from one boundary of the transducer to another (the direction being from the top to the bottom of the pillars 74 in FIG. 7*b*), and "3" indicates the number of directions in which the filler material is continuous from one boundary of the transducer to another (the directions being horizontally and vertically in FIG. 7 and vertically in FIG. 7*b* ). The composite bar is then diced into individual transducer elements along the cut lines 80**.

However, the present inventor has noted that it is difficult to maintain a uniform element pitch along the length (horizontally in the drawings) of the array 70 while maintaining the dicing cuts or kerfs 80 in registration with the interstices 72 of the composite, as shown in the drawings. In part this is due to the fact that most filler materials are known to shrink during curing, changing the dimensions of the bar. In accordance with a further aspect of the present invention, the present inventor orients the composite material pattern at a non-parallel, non-orthogonal orientation to the array kerfs as shown in FIGS. 8 and 9. The bars of composite material shown in these drawings are formed by subdicing a plate of piezoelectric material and filling the interstices thus formed, then cutting out the bar of array composite from the composite plate at the desired angle to the composite pattern. In FIG. 8 the element dicing cuts 80 of transducer array 90 are at a 45° angle to the pattern of the rows of pillars 94 and filler interstices 92, and in FIG. 9 the element dicing cuts 80 of transducer array 100 are at a 15° angle to the pattern of the rows of pillars 104 and filler interstices 102. The oblique orientation of the pattern of the composite material and the kerfs provides a performance advantage, in that the modes of lateral resonance of the array elements are no longer aligned with those of the subelements. Thus, the lateral propagation of lamb waves and lateral resonances which cause ringing in elements of the array is strongly suppressed by this oblique orientation of the array elements and composite pattern.

Figures 11A, 11B, 11C:
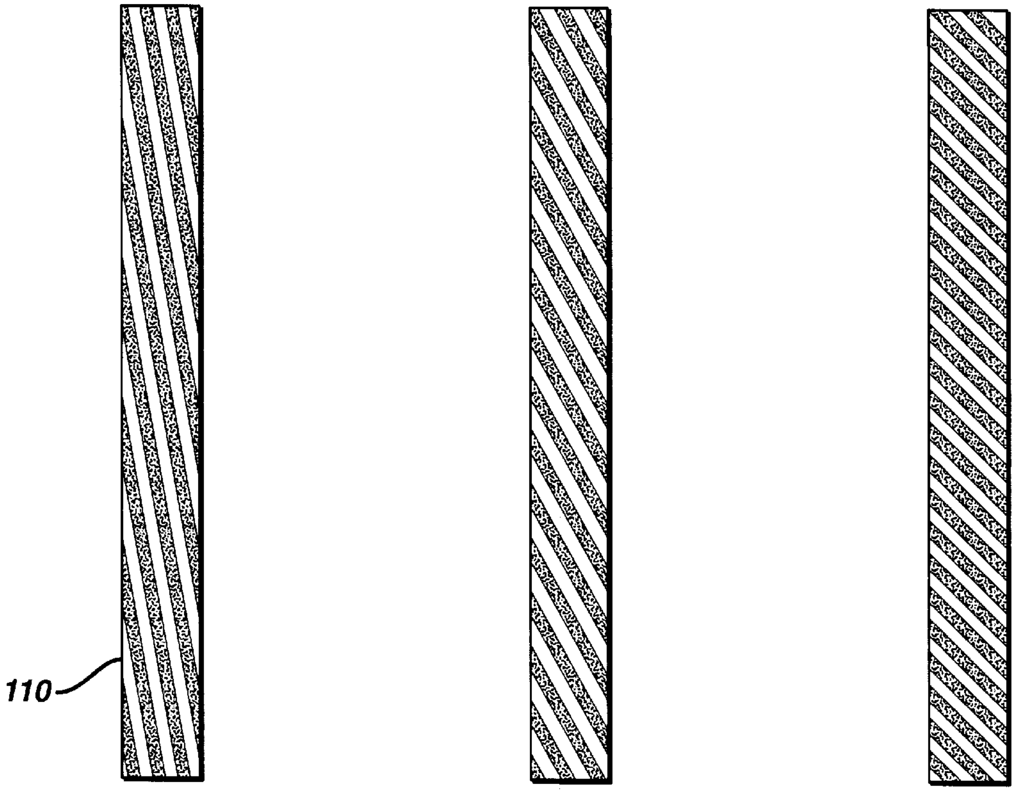
Figure 12:
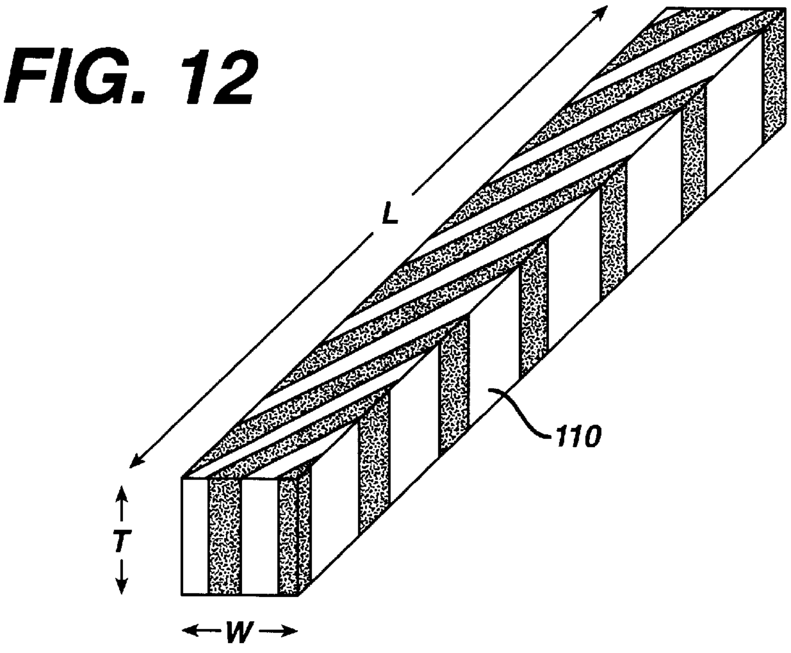

FIGS. **10*a*–12 illustrate this oblique orientation for 2—2 composite transducer elements, in which each drawing depicts a single element of a composite transducer array. In these drawings, the shaded stripes represent composite filler and the white stripes represent piezoelectric material. In FIGS. 10*a* and 10*b* the pattern of the 2—2 composite is at the conventional 0° and 90° angles to the kerf cuts, which in these drawings are the vertical sides of the elements. In FIGURE 11a the composite pattern of the element 110 is at a 10° angle to the side kerfs, in FIG. 11***b* the angle is 25°, and in FIGURE 11*c* the angle between the composite pattern and the sides of the element is 45°. Arrays with shallower angles have been found most easy to conform for a curved transducer array. The element 110 of FIG. 11*a* is shown in a perspective view in FIG. 12, where L is the width of the element along the kerf cut, T is the thickness of the element, and W is the width of the element. The composite element provides another benefit which is apparent in this drawing. It is seen in FIG. 12 that the width W and thickness T of the element have approximately the same dimension. If this were a conventional entirely ceramic piezoelectric element, the resonance modes in the T and W directions would be approximately the same due to the similarity of these dimensions. Since the element is intended to have a dominant resonance in the T direction, the direction of ultrasound transmission, the element would have to be subdiced to increase its lateral resonant frequency. The subdicing cut would result in two subelements, each with a dimension of L, T, and slightly less than W/2 in the width dimension. However, such subdicing is not necessary for the element shown in FIG. 12, as each piezoelectric subelement of the composite, in combination with the selected subelement angle of the composite, already exhibits the preferred height T to width W ratio. That is, the T dimension of each composite piezoelectric subelement is already in excess of its W dimension. Since the elements of the array do not need to be subdiced, the resulting array is more rugged and less expensive to fabricate than a comparable subdiced array.

Figure 13A:
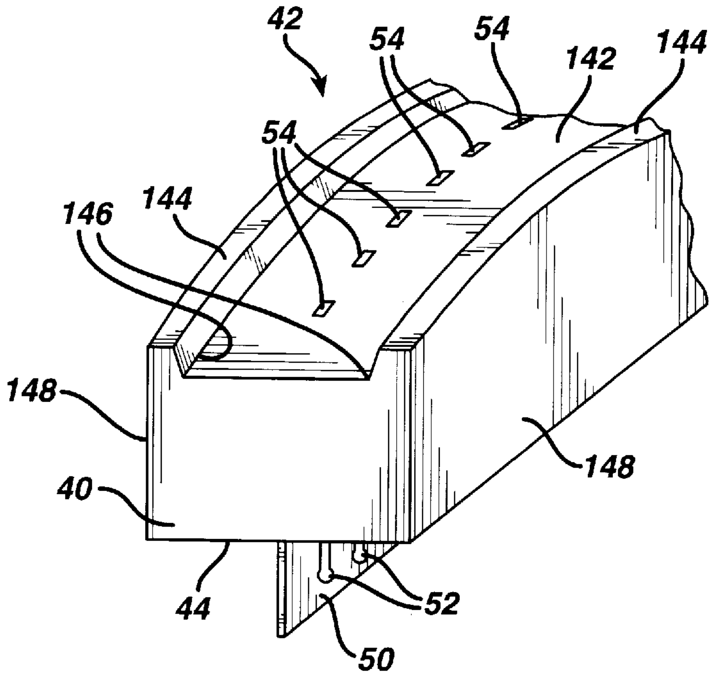

FIGS. 13*a*–13*d* illustrate different stages of construction of a convex array in accordance with the principles of the present invention. FIG. 13*a* illustrates a backing block 40 in which a flex circuit 50 has been embedded. The proximal end of the flex circuit is seen extending from the proximal end 44 of the block 40. Conductive traces 52 of the flex circuit terminate at distal ends 54 on the distal surface 42 of the block 40. The distal surface has been ground and lapped to form a central floor surface 142 with which the distal ends 54 of the conductive traces are aligned. The floor surface 142 is bounded on either side by a shoulder 144. The block 40 is prepared for the transducer array by coating the floor surface 142, the shoulders 144, and the lateral sides 148 of the block with a metallic adhesion layer and then a gold coating. The adhesion layer and gold coating are then scored at the junctures 146 of the shoulders with the floor surface to electrically isolate the floor surface from the gold coating on the shoulders 144 and lateral sides 148. The distal ends 54 of the conductive traces are in electrical contact with the gold coating on the floor surface 142.

Figure 13B:
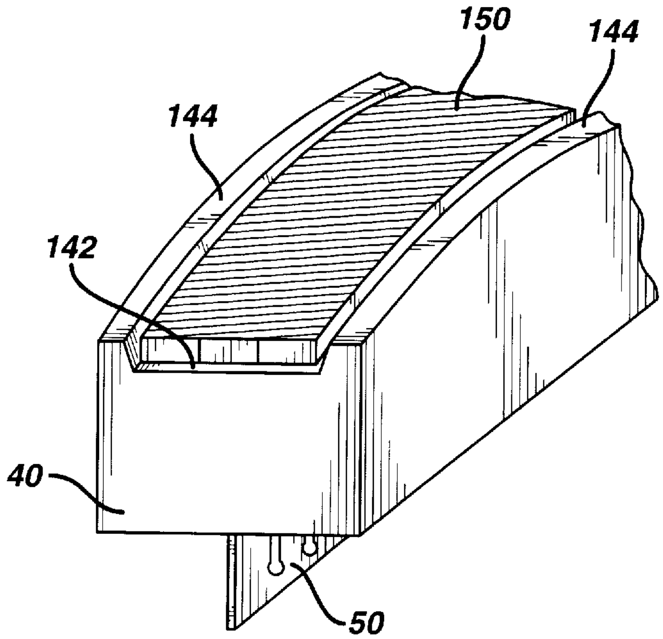

A composite array transducer is prepared, coated with gold on both its top (emitting and receiving) side and bottom (floor surface facing) side, and conformed to the shape of the convex arc of the floor surface 144. In FIG. 13*b* the transducer array 150 comprises a 2—2 composite with a 10° orientation between the pattern of the composite material and the kerf locations (see FIGS. 11*a* and 12). The composite array bar 150 is readily conformed to the intended convex arc.

Figure 13C:
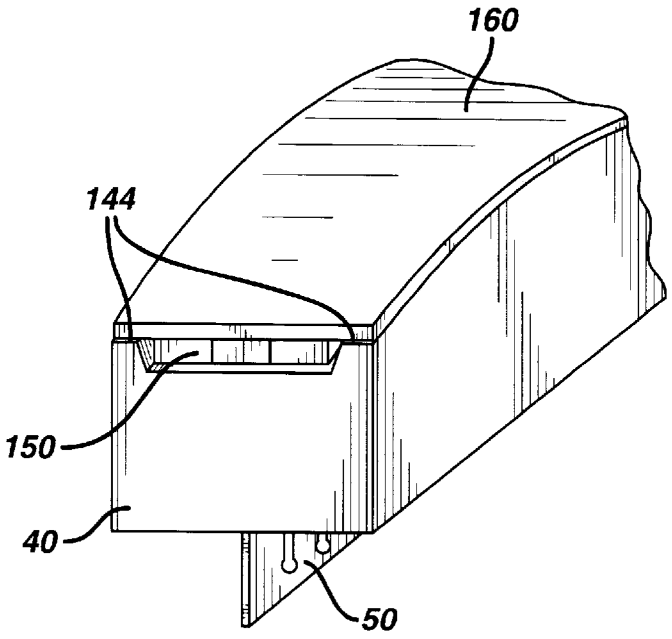

The gold coated surfaces of the composite array bar 150 are lightly coated with a low viscosity adhesive and the bar 150 is then set on the floor surface 142 of the backing block 40 as shown in FIG. 13*b*. The ends of the bar 150 which oppose the side shoulders 144 are not in contact with either of the adjacent shoulders 144. An acoustic matching layer sheet 160 is then placed across the top surface of the array and the shoulders 144 as shown in FIG. 13*c*. The characteristics of the sheet 160 are chosen to provide the desired acoustic impedance matching. Kapton has been found to be one suitable material for sheet 160. The side of the sheet 160 is coated with gold and makes contact with the adhesively coated, gold coated top surface of the transducer array 150. Pressure is then applied to the backing block 40 and the sheet 160 to compress the adhesively coated array 150 between the floor surface and the matching layer sheet 160, thereby squeezing excess adhesive from between the gold coated surfaces and achieving electrical contact between the gold surfaces. The sides of the sheet 160 are also adhesively attached to the top surfaces of the shoulders 144. The adhesive is then allowed to cure.

Figure 13D:
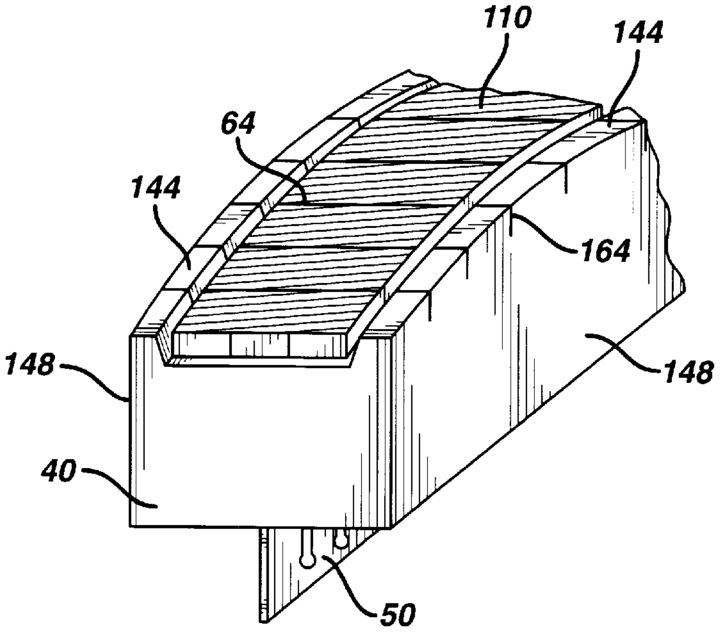

The transducer array bar 150 is diced into separate transducer array elements 110 by cutting through the matching layer sheet 160, transducer bar 150, and the surrounding shoulders 144, as shown in FIG. 13*d*. In this drawing the matching layer sheet 160 is not shown so that the diced array elements 110 can be clearly seen. The dicing cuts 64 extend through the gold coating on the floor surface 142 to separate the coating into separate electrical areas for each element 110 and its conductive trace 52,54. The dicing cuts also extend through the shoulders 144 as shown at 164. However, the tops of the transducer elements are all electrically connected to the gold coating on the underside of the matching layer sheet 160, which in turn is electrically connected to the gold coating on the tops of the shoulders 144 and to the gold coating on the sides 148 of the block 40. Thus, a ground potential can be applied to the top surfaces of all of the transducer elements 110 by connecting a ground lead to the sides 148 of the backing block 40, while the bottom surface of each transducer element 110 is connected to its own conductive trace 52 for the application of excitation potentials and reception of echo signals.

What is claimed is:

1. A prefabricated backing block for subsequent attachment to an ultrasonic array transducer comprising a flexible circuit board having a plurality of conductive traces formed thereon in a pattern corresponding to a predetermined array element spacing which is embedded in a body of acoustic backing material, said conductive traces extending to a distal, array contacting side of said body at which said traces are immobilized and aligned for making electrical connection with elements of an array transducer at the surface of said array transducer which is affixed to said array contacting side of said body, and said conductive traces extending out from a second, proximal side of said body for connection to electrical circuitry.

2. The backing block of claim 1, wherein said flexible circuit board extends substantially orthogonally to said distal side of said body.

3. The backing block of claim 1, wherein said conductive traces extend to electrical connection points on said flexible circuit board outside of said body.

4. The backing block of claim 1, further including at least one additional flexible circuit board having a plurality of conductive traces formed thereon and embedded in said body of acoustic backing material for making electrical connection to a different group of transducer elements than those connected to the conductive traces of said first named flexible circuit board.

5. The backing block of claim 1, wherein said flexible circuit board does not extend to said distal side of said body adjacent to said conductive traces.

6. The backing block of claim 1, wherein said distal, array contacting side is coated with a conductive electrode material.

7. The backing block of claim 6, wherein said conductive electrode material is separated into individual electrodes at the time of dicing of the transducer array.

8. A prefabricated backing block for subsequent attachment to an ultrasonic array transducer comprising a flexible circuit board having a plurality of conductive traces formed thereon which is embedded in a body of acoustic backing material, said conductive traces extending to a distal, array contacting side of said body for making electrical connection with the elements of said array transducer, and extending to a second, proximal side of said body for connection to electrical circuitry, wherein said distal, array contacting side of said body is convexly curved.

9. A prefabricated backing block for subsequent attachment to an ultrasonic array transducer comprising a flexible circuit board having a plurality of conductive traces formed thereon which is embedded in a body of acoustic backing material, said conductive traces extending to a distal, array contacting side of said body for making electrical connection with the elements of said array transducer, and extending to a second, proximal side of said body for connection to electrical circuitry, wherein said distal, array contacting side is coated with a conductive electrode material, and wherein said distal side is formed into a central depression with opposing shoulders into which depression said array transducer is mounted.

10. The backing block of claim 9, wherein said shoulders are connected to a reference potential.

11. The backing block of claim 10, further comprising a matching layer, extending across said shoulders and having a reference electrode surface contacting the patient facing surface of said transducer array.

* * * * *